(12) United States Patent
Kelly et al.

(10) Patent No.: US 8,357,392 B2
(45) Date of Patent: Jan. 22, 2013

(54) DRY ANTISEPTIC WIPES COMPRISING AN AMPHOTERIC SURFACTANT

(76) Inventors: Albert R Kelly, Douglaston, NY (US); Lowell Safertein, West Orange, NJ (US)

(*) Notice: Subject to any disclaimer, the term of this patent is extended or adjusted under 35 U.S.C. 154(b) by 0 days.

(21) Appl. No.: 13/297,343

(22) Filed: Nov. 16, 2011

(65) Prior Publication Data

US 2012/0055510 A1    Mar. 8, 2012

Related U.S. Application Data

(63) Continuation of application No. 12/803,495, filed on Jun. 30, 2010, now abandoned, which is a continuation-in-part of application No. 12/589,820, filed on Oct. 30, 2009, now abandoned, which is a continuation-in-part of application No. 11/118,197, filed on May 2, 2005, now abandoned.

(51) Int. Cl.
| | |
|---|---|
| *A61K 9/70* | (2006.01) |
| *A61K 31/74* | (2006.01) |
| *A61K 33/18* | (2006.01) |
| *A01N 25/30* | (2006.01) |
| *A01N 25/34* | (2006.01) |
| *A01N 25/08* | (2006.01) |
| *C11D 3/48* | (2006.01) |

(52) U.S. Cl. .................. 424/443; 424/78.02; 424/78.07; 424/405; 424/409; 424/672; 442/123; 442/171; 510/131; 510/391; 510/438

(58) Field of Classification Search ........................ None
See application file for complete search history.

*Primary Examiner* — Kevin S Orwig
(74) *Attorney, Agent, or Firm* — Evelyn M. Sommer

(57) ABSTRACT

A personal skin cleansing wipe comprising a flexible substantially dry matrix formed from synthetic, woven, non-woven or knitted fibers impregnated with a substantially anhydrous antimicrobial, antiseptic, antifungal solution in an amount wherein the matrix retains its substantially dry characteristics and the treatment solution includes an amount of PVP-iodine as active in solution in glycol and or glycerin. The treatment solution, in addition to an effective amount of PVP-iodine as active, contains surfactants, preferably Tego® Betaine CK D, and optionally a compatible fragrance and/or moisturizer. The wipe is activated with water just prior to use.

13 Claims, No Drawings

DRY ANTISEPTIC WIPES COMPRISING AN AMPHOTERIC SURFACTANT

CROSS-REFERENCE TO RELATED APPLICATION

This application is a continuation of application Ser. No. 12/803,495 filed Jun. 30, 2010 (now abandoned), which is a continuation-in-part of application Ser. No. 12/589,820 filed Oct. 30, 2009 (now abandoned), which in turn is a continuation-in-part of application Ser. No. 11/118,197 filed May 2, 2005 (now abandoned).

FIELD OF INVENTION

The present invention relates to a personal skin-cleansing wipe incorporating a non-aqueous solvent, a surfactant, and an antimicrobial/antifungal/antiseptic component. The wipe contains PVP-iodine as active component which is incorporated in substantially anhydrous form. The wipe is activated by the addition of water before use and residual debris, including PVP-iodine remaining on the skin following use is removed by rinsing with water. The structure of the wipe should preferably comprise synthetic fibers. The wipe can be used as an antiseptic hand washcloth, an antifungal body or skin wipe or for first aid or wound cleaning, among other applications.

BACKGROUND OF THE INVENTION

It is well known that topical skin surfaces of humans, from time to time, need to be cleaned and desirably, sanitized.

Currently, there are only two over-the-counter antimicrobial active ingredients enjoying unqualified approval by the U.S. Food and Drug Administration for use in antiseptic skin cleansing, for first aid and wound cleansing, and in antifungal cleansing wipes.

The first, ethyl alcohol, has a long history of safe and effective use. However, there is a long list of negative attributes associated with the use of the ethyl alcohol. It dries and irritates healthy skin and stings injured or abraded skin. Moreover, as ethyl alcohol is highly volatile, it dissipates rapidly if not packaged in a proper barrier container.

Other disadvantages of ethyl alcohol include its stringent regulation by governmental agencies, its ability to erode some metals, its tendency to remove paint and varnish and to delaminate some plastics.

The other approved antimicrobial ingredient is PVP-iodine (also called Povidone-iodine), which is a stable complex of polyvinylpyrrolidone (PVP) and elemental iodine. While elemental iodine has been used in antiseptic applications (U.S. Pat. No. 4,045,364), elemental iodine is known to possess a number of undesirable properties. Free elemental iodine is highly toxic, irritative, sensitizing, odorous and it also causes stains and readily vaporizes due to sublimation. U.S. Pat. No. 2,739,922 teaches the complex of PVP and iodine, which possesses reduced objectionable properties and increased bactericidal activity as compared to free elemental iodine. PVP-iodine has a variety of uses in health care on both skin and hard surfaces as an effective germicide, bactericide, fungicide, virucide, and amebicide.

The use of pre-moistened wipes to deliver aqueous solutions containing alcohol or PVP-iodine to sanitize skin or to disinfect hard surfaces is longstanding. But such wet wipes are expensive because they require barrier packaging to prevent evaporation or "dryout". Also contributing to the expense of such wipes is the need for special binder-free substrates for hydro-alcoholic formulations and starch-free substrates for aqueous iodophor formulations. Thus, the use of these ingredients has been limited and reserved for higher risk healthcare and medical environments where other considerations justify the higher costs.

U.S. Pat. No. 2,599,140 discloses an iodine-containing detergent using iodine dissolved in a mixture of polyalkylene glycol and glycerin to prevent fast evaporation of elemental iodine. U.S. Pat. No. 4,355,021 discloses a substantially dry virucidal wipe using a flexible paper substrate, having iodine stabilized in polyoxyethylene (40) sorbitol septaoleate. U.S. Pat. No. 4,045,364 discloses dry disposable paper tissues impregnated with elemental iodine or PVP-iodine, which can be packaged and stored for long term without undue deterioration. U.S. Pat. No. 5,919,471 discloses a substantially flexible, dry and antiseptic wipe impregnated with PVP-iodine present in at least one glycol compound.

SUMMARY OF THE INVENTION

The present invention is focused on an antiseptic skin-cleansing washcloth, or an antimicrobial/antifungal skin-cleansing wipe. The wipe is manufactured as a dry matrix into which PVP-iodine and one or more surfactants, in a waterless formulation are mechanically impregnated using glycols as diluents. The matrix can comprise synthetic, woven, non-woven or knitted fibers. In use, the treated dry matrix is wetted with water and the wet matrix is rubbed on skin to develop a foaming and cleansing formulation which when rinsed washes away residual debris and PVP-iodine with no evident staining or discoloration.

DETAILED DESCRIPTION OF THE INVENTION

The presence of water is essential in all cleaning applications, such as hand cleansing. However, if these antiseptic wipes containing PVP-iodine as active were supplied in wet form, the activated iodine risks rapid degradation in the presence of water, and the aqueous iodine would leave visible stains on skin, clothing or hard surfaces. These disadvantages not only discourage use but also add to the cost of packaging, storing and using the wipes, and most importantly, reduce their shelf life time. It has now been found that wipes containing PVP-iodine can be manufactured using an anhydrous formulation that will yield substantially dry wipes that can be activated with water shortly before use by the end user.

The synthetic matrix is manufactured dry, meaning no water has been added other than the water naturally present in the basic fibers. Typically, these synthetic materials have a moisture content of less than 1%. The term "dry" also encompasses a finished product, i.e., a wipe into which the anhydrous treatment solution containing an antimicrobial and surfactant formulation has been impregnated. The matrix with the treatment solution normally feels dry, and lubricious to the touch.

The matrix for containing the anhydrous treatment solution used in the present invention comprises synthetic fibers which may be processed into woven, non-woven or knitted form. Of particular interest for use in the invention are the following fibers: polypropylene, polyester, and blends of these fibers and other synthetics.

In accordance with the invention, PVP-iodine is the antiseptic active. Commercially, PVP-iodine complex is available in a pharmaceutical grade containing 10 parts active halogen per 100 parts of dry powder. For this reason, the commercial product has sometimes been referred to as "PVP-iodine 10." There are two major suppliers of PVP-iodine:

BASF Fine Chemicals and Napp Technologies. PVP-iodine is completely soluble in cold water with mild agitation as well as propylene glycol in amounts up to and exceeding 10% (1.0% available iodine). Aqueous solutions of PVP-iodine have been marketed under the trademark Betadine® microbicides by Purdue Frederick Company as a defense against topical infection from pre-surgical scrubbing for hand and skin degerming, as being active against both gram-positive and gram-negative bacteria, fungi, protozoa and viruses in vivo.

In general, to reduce microorganisms on skin and prevent infections, topical solutions containing between about 1 and 15% PVP-iodine (0.1 and 1.5% available iodine) may be used. It is preferred that the solution contain between about 5 and 10% PVP-iodine (0.5 and 1% available iodine) and most preferably between about 7.5% and about 10% PVP-iodine (0.75% and 1.0% available iodine).

The substrate comprises synthetic, woven, non-woven or knitted fibers, or blends thereof. The intended use (hands, body, first aid) dictates that amount of add-on needed to achieve effective skin antisepsis. The matrix is uniformly coated with variable amounts of treatment solution expressed as a percentage of the basis weight of the substrate up to a maximum of about 40% by weight of the substrate.

The treatment solution also contains from about 0.5% to 25% by wt. of a non-ionic or cationic surfactant, and preferably about 5% to about 15% by wt. The non-ionic or cationic surfactant is present in an amount of less than about 40% by weight of the matrix. The specific amount of the particular non-ionic and/or cationic surfactant which is employed within this range will depend upon the detergent activity desired as can be readily determined by one of ordinary skill in the art. Any of the well-known classes of non-ionic and cationic surfactants such as nonylphenol ethoxylates, also known as Igepal, may be employed in the wipe of the present invention. The presence of amphoteric surfactant enhances skin cleaning efficiency. The amphoteric surfactant is present in an amount of about 0.5% to 25% by wt. If the surfactant comprises a combination of nonionic and/or cationic and/or amphoteric surfactant, the total amount of surfactant will amount to about 25% by wt. of the treatment solution.

Amphoteric or zwitterionic surfactants contain two charged groups of a different sign. Whereas the positive charge is almost always ammonium, the source of the negative charge may vary (carboxylate, sulphate, sulphonate). There can be cationic (positively charged) or non-ionic (no charge) surfactants in solution, depending on the acidity or pH of the treatment solution.

The amphoteric surfactants are very mild, making them particularly suited for use in personal care and household cleaning products. They are also used in hand dishwashing liquids because of their high foaming properties. Amphoteric surfactants are compatible with all other classes of surfactants and are soluble and effective in the presence of high concentrations of electrolytes, acids and alkalis.

The advantage of using a water-free amphoteric surfactant is that povidone iodine is stable in the presence of these high-foaming surfactants. On the other hand, povidone iodine is not stable in the presence of high foaming anionic surfactants. Cationic surfactants tend to be low foamers and non-ionic surfactants are generally for industrial applications and are low in foaming properties.

A preferred instance of an amphoteric surfactant is cocamidopropyl betaine, the IUPAC name of which is {[3-(dodecanoylamino)propyl](dimenthyl)ammonio}acetate and CAS number is 86438-79-1. Its structure is shown below:

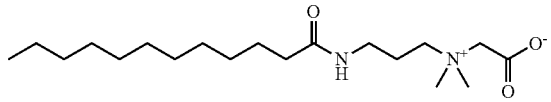 [SMILES: CCCCCCCCCCCC(=O)NCCC[N+](C)(C)CC(=O)[O-]]

Cocamidopropyl betaine is classed as a semi-synthetic surfactant/foaming agent. Cocamidopropyl betaine (CAPB) is made from coconut oil reacted with chemicals and is a zwitterionic surfactant with a quaternary ammonium cation in its molecule. The product Tego®0 Betaine, a spray dried form of cocamidopropyl available from Evonik has been used as a surfactant in bath products like shampoos and hand soaps, and in cosmetics as an emulsifying agent and thickener, and to reduce irritation purely ionic surfactants would cause. It also serves as an antistatic agent in hair conditioners. Tego® Betaine CK D is the preferred surfactant for use in preparing the treatment solutions of the invention to be used for impregnating the non-woven substrates.

Cocamidopropyl betaine is a derivative of cocamide and glycine betaine (a form of betaine). Cocamidopropyl betaine is a medium strength surfactant which most often does not irritate skin or mucous membranes. Some studies indicate it is an allergen. It also has antiseptic properties, making it suitable for personal sanitary products. It is compatible with the other cationic and nonionic surfactants. The dissolution of Tego® Betaine CK D in propylene glycol has not heretofore been disclosed. The literature references all disclose water dilutions of various concentrations and it is in this form that it is conventionally obtained from its suppliers.

The sole supplier of spray dried cocamidopropyl betaine is Evonik Industries under the trade name of Tego® Betaine CK D. The use of Tego® Betaine CK D as an anhydrous surfactant is preferred because it does not precipitate the release of free iodine and thereby risk depletion of the effectiveness of the treatment solution before use.

Other amphoterics include but are not limited to cocobetaine lauryl dimethyl cabroxymethyl betaine, lauryl dimethyl alpha-carboxyethyl betaine, cetyl dimethyl carboxymethyl betaine, lauryl bis(2-hydroxypropyl) alpha-carboxy ethyl betaine, cocodimethyl sulfopropyl betaine, myristyl amidopropyl betaine, sodium lauroamphoacetate, sodium alkylaminopropionate and sodium capryloampho hydroxypropyl sulfate. The preferred cocamidopropyl betaine is the one just described because of its superior solubility properties in propylene glycol and the resultant improved effectiveness of the combination with povidone iodine in the propylene glycol. In this connection, it has been observed by the inventors herein that the solution formed by dissolving the spray dried Tego® Betaine CK D in propylene glycol has per se anti-microbial activity.

Tego® Betaine CK D as supplied by Evonik Industries is a fatty acid amido alkyl betaine and is supplied as a pale yellow powder which is soluble in water and unexpectedly found by the inventors herein to also be soluble in propylene glycol. The product is made from a 30% aqueous solution of cocamidopropyl betaine by spray drying. Spray drying is a method of producing a dry powder from a liquid or slurry by rapidly drying with a hot gas. This is the preferred method of drying of many thermally sensitive materials such as foods and pharmaceuticals. A consistent particle size distribution is a reason for spray drying some industrial products such as catalysts. Air is the heated drying media; however, if the liquid is a flammable solvent such as ethanol or the product is oxygen-sensitive then nitrogen is used.

The spray dryer takes a liquid stream and separates the solute or suspension as a solid and the solvent into a vapor. The solid is usually collected in a drum or cyclone. The liquid input stream is sprayed through a nozzle into a hot vapor stream and vaporized. Solids separate as moisture quickly leaves the droplets. A nozzle is usually used to make the droplets as small as possible. Droplet sizes can range from 20 to 180 µm.

The dry article optionally may contain one or more fragrances for imparting a pleasant odor to the skin. As used herein, the term "fragrance" includes chemicals that can mask unpleasant odors and/or destroy unpleasant odors. When employed, the fragrance is present in the dry wipe in amounts up to 2% by wt. of the treatment solution.

The present invention uses a non-aqueous solvent carrier for PVP-iodine during the manufacturing and storage of the wipes. Glycols are preferred as non-aqueous solvents and propylene glycol is the preferred glycol. The non-aqueous solvent functions primarily to dissolve the PVP-iodine and the anhydrous surfactant, and also imparts emollience and lubricity to the treatment solution which helps prevent skin breakdown and maintain skin softness.

The use of propyl glycol instead of water as a solvent is essential. Propylene glycol does not precipitate the release of free iodine, and thereby deplete its effectiveness before its actual use. Propylene glycol, unlike water, actually preserves the stability of PVP-iodine and facilitates an extended shelf life of the treated wipe. Propylene glycol is a lubricious emollient imparting soothing and softening qualities to skin. Further, propylene glycol does not freeze in cold weather. The use of propylene glycol as a non-aqueous solvent obviates the need for buffers, stabilizers and preservatives, which are generally required to be used in aqueous solutions.

Propylene glycol is an active skin lubricant and emollient as well as the solvent for the PVP-iodine and the Tego® Betaine CK D. Typically, propylene glycol is the major component in the treatment solutions of the present invention. However, it can also be combined with similar glycols such as glycerin or low molecular weight polyethylene glycols such as PEG-200, PEG-400, etc. Preferably, not more than about 40% by wt. of the propylene glycol is replaced with these other glycols or glycerine.

The matrix is prepared in accordance with one of the methods described above, from which the cleaning wipe or other products of the present invention are obtained, is preferably coated and impregnated with the non-aqueous treatment solution using adaptations of the conventional slot coating process.

Slot die coating is used to accommodate the critical need for a controllable and more efficient coating method. This process has been successful in replacing other coating methods for applying many types of solutions. A slot coating die is a device that is capable of maintaining a fluid's temperature, distributing a fluid uniformly and defining a coating width. The die is comprised of stainless steel body sections that define the fluid flow chamber. Slot die coating has four main advantages: (1) increased production speeds; (2) positive coat weight control; (3) cross-web distribution control; and (4) improved waste management.

The superior control over the coating application as provided by the slot die method is attributable to its constant application rate. An extruder or positive displacement pump feeds the coating fluid into the die at a pulse-free, uniform rate, and all of the fluid that goes into the die is applied to the web. In roll coating, only a portion of the coating on the applicator roll is actually deposited on the web. The amount varies with such factors as the viscosity of the fluid, the speed of the web and the speed of the rolls.

The slot-coating die differs from embossed coating in two critical respects: (1) it is a "pre-metered system that applies a coating to the web at a constant rate and permits precise control over coat weight and cross-web distribution, reducing waste, allowing higher line speeds, and increasing product quality and uniformity; and (2) it is an enclosed system, reducing emission of volatiles and preventing airborne contamination.

The treated matrix, containing the measured volume of treatment solution is cut and folded on line into the desired product form that is saleable as a manufactured product and ready for distribution.

The slot coating/impregnation method described above enables a uniform and accurate application of all active ingredients to the woven or non-woven matrix of natural and/or synthetic fibers without the use of carriers and without the need for a separate step to dry the residual diluted solutions from the matrix.

Prior to use by the end users, the wipes are wetted with water. The presence of the water is needed to effect the release of free iodine for efficient antisepsis and skin cleansing performance. The exclusion of water from the treatment formulation, which is applied to the substrate during manufacturing, provides the many benefits described above in the manufacturing, storage and distribution of the wipe products.

The following examples are given in order to more completely illustrate the usage benefits of the invention, and are not to be construed in limitation thereof:

EXAMPLE #1

Formulation #1 listed below was impregnated into a 4.0 oz./sq. yd. non-woven 100% polypropylene needle-punched fabric at a level of 22.7%-25.7% add-on of the web. Wipes of 8×11 inches were cut from the fabric and were prepared using the technique described in U.S. patent application Ser. No. 10/021,395.

| Treatment of Wipes | | |
| --- | --- | --- |
| Weight of wipes (g.) | Add-on (g.) | % add-on |
| 7.4 | 1.9 | 25.7 |
| 7.7 | 1.8 | 23.4 |
| 7.9 | 1.8 | 22.8 |

| Formulation # 1 | |
| --- | --- |
| Wt. Percent | Ingredients |
| 6.3% | Povidone iodine |
| 30% | BIO-SOFT EA 10 (100% water-free concentration manufactured by Stepan) |
| 47.2% | Propylene glycol |
| 15% | Glycerine |
| 1.5% | Menthol fragrance |

Evaluation

The treated antiseptic hand wipes were evaluated by wetting both hands with water under a running faucet. The wet hands were then rubbed with the dry wipe to activate the ingredients. The wipe foamed readily when activated with water from the wet hands. There was very little iodine odor detected, and the cleansing action of the wipe was quickly evident. There was no irritation and there was a lubricious feel as the wet wipe was rubbed over the hands. The weight of water extracted from the saturated wipe was between 5-7 grams of water remaining from the wetting. This would produce an iodine concentration of about 1900-PPM. After a few minutes, the wipe was discarded and the hands were rinsed under water. There was no staining on the hands, which felt soft and refreshed with a pleasing aroma.

EXAMPLE #2

The 4.0 oz./sq. yd. needle-punched 100% polypropylene 8×11-inch fabric was similarly impregnated with formulation #2 listed below:

| Formulation # 2 | |
| --- | --- |
| Wt. Percent | Ingredients |
| 5% | Povidone iodine |
| 20% | Glycerine |
| 20% | Igepal Co-530 (100% water-free concentration manufactured by Stepan) |
| 53.5% | Propylene glycol |
| 1.5% | Menthol fragrance |

| Treatment of Wipes | | |
| --- | --- | --- |
| Weight of wipes (g.) | Add-on (g.) | % add-on |
| 7.7 | 1.1 | 14.2 |
| 7.7 | 1.3 | 16.8 |

Evaluation

A wipe was lightly moistened with water from a faucet. The wet wipe, which picked up 25 grams of water, was rubbed gently over the hands for one minute. The wipes foamed extensively as the hands were gently scrubbed with the wipe. No odor of iodine was detected. A lubricous feel was detected as the wipe was used on the hands. The wipe was then discarded and the hands were rinsed under water. No staining of the hands was observed and the hands felt smooth, soft and clean with a pleasant aroma. Based on the water pick-up of the wipe, the iodine concentration was about 220-PPM. Substantially identical results to those obtained in Example 1 were observed.

EXAMPLE #3

1.5 oz./sq. yd. thermo-bonded polypropylene fabric was cut into 8×10-inch wipes. Wipes were treated with formulation #3 listed below:

| Formulation # 3 | |
| --- | --- |
| Wt. Percent | Ingredients |
| 58.0% | Propylene glycol |
| 25% | Igepal CO-530 (100% water free concentration manufactured by Stepan) |
| 5.0% | Povidone iodine |
| 12.0% | Glycerine |

| Treatment of Wipes | | |
| --- | --- | --- |
| Weight of wipes (g.) | Add-on (g.) | % add-on |
| 2.5 | 0.50 | 20.0 |
| 2.6 | 0.40 | 15.43 |
| 2.6 | 0.50 | 19.2 |

Evaluation

Hands were wet under a running faucet. A treated wipe was rubbed over the wet hands. Foaming was observed within seconds. The wipe was easy to manipulate through the hands and cleaned the hands thoroughly. After 30 seconds, the wipe was discarded and the hands rinsed under water. No staining of the hands was observed. Hands felt refreshed and soft. It could be demonstrated that the treatment solution was effective as an antimicrobial.

EXAMPLE #4

Formulation #4 listed below was impregnated into nonwoven, needle-punched material obtained from NonWoven Solutions (NWS), grade A #1021030-16.75 C, 70 gsm, 100% PET material. The treated roll goods were cut to a preferred size of 8.375×6.0 inches. The 35% add-on of treatment solution amounted to 0.8 grams of treatment solution per wipe. The preferred add-on for this dry wipe weighing 2.3 grams ranges from 0.5 grams (22%) to 0.9 grams (39%) per wipe.

| Formulation # 4 | |
| --- | --- |
| Wt. Percent | Ingredients |
| 5.0% | Povidone iodine |
| 79.0% | Propylene glycol |
| 16.0% | Cocamidopropyl betaine (Tego ® Betaine CK D) |

This formulation was prepared as follows: 40 pounds of propylene glycol were introduced into a 10-gallon stainless steel drum. A heating band was attached around the drum and the drum was heated to 80° F. An air driven stirrer provided in the drum stirs the propylene glycol gently.

A total of 3,677.4 grams of Tego® Betaine CK D was then added to the drum in 10 increments over a 50-minute time period.

When all of the Tego® Betaine was in the solution, the temperature was increased to 100° F. and a total of 1,148.6 grams of povidone iodine were introduced into the solution in five, five-minute increments. After the last addition of the povidone iodine, the solution was stirred for another 30 minutes.

| Chemicals | Pounds | Wt. Percent | Grams |
|---|---|---|---|
| Propylene glycol | 40.0 | 79.0% | 18,160 |
| PVP iodine | 2.53 | 5.0% | 1148.6 |
| Tego ® Betaine CK D | 8.10 | 16.0% | 3,677.4 |
| TOTAL | 50.63 | 100% | 22,986.0 |

The treated wipes were tested for germicidal activity using the Rapid Germicidal Activity: Time Kill Procedures method, in which a standard quantity of a bacteria is applied to the wipe and the percent reduction in viable bacteria is measured at 1 minute and 5 minute contact times. The control was an untreated wipe. The results of the studies follow:

Control Wipe (Untreated)

| | Percent Reduction | |
|---|---|---|
| Micro-organism | 1 minute | 5 minutes |
| Staphylococcus Aureus ATCC # 6538 | 0.0% | 9.288% |
| Staphylococcus Aureus ATCC # 33592 | 5.739% | 1.515% |
| Escherichia coli ATCC # 11229 | 41.068% | 40.056% |

Treated Wipe

| | Percent Reduction | |
|---|---|---|
| Micro-organism | 1 minute | 5 minutes |
| Staphylococcus Aureus ATCC # 6538 | >99.99% | >99.99% |
| Staphylococcus Aureus ATCC # 33592 | >99.99% | >99.99% |
| Escherichia coli ATCC # 11229 | >99.99% | >99.99% |
| Klebsiella Pneumonia ATCC # 10031 | >99.99% | >99.99% |
| Pseudomonas Aueroginosa | 99.894% | 99.971% |

EXAMPLE #5

The same 70 GSM, needle-punched non-woven material, cut to the same dimensions as in Example #4, was slot-coated with 0.6 grams of formulation #5, but the concentration of povidone iodine in this formula was increased by 50%, from 5% to 7.5%, as indicated below.

36.17 pounds of propylene glycol were introduced into a 10-gallon stainless steel drum. A heating band was attached around the drum and the drum was heated to 90° F. An air driven stirrer provided in the drum stirs the propylene glycol gently.

A total of 7 pounds of Tego® Betaine CK D were then added to the drum in increments over a 90-minute time period. The solution formed was clear yellow in color after the addition of the Tego® Betaine CK D.

The temperature of the solution was raised to 110° F. and 3.5 pounds of povidone iodine were added in increments over a 60-minute time period. The solution was stirred for an additional 15 minutes after the addition of all of the povidone iodine. The final solution was dark red in color.

| Formulation # 5 | | | |
|---|---|---|---|
| Ingredients | Wt. Percent | Pounds | Grams |
| Povidone iodine | 7.5% | 3.5 | 1,589 |
| Propylene glycol | 77.5% | 36.17 | 16,421 |
| Cocamidopropyl betaine (Tego ® Betaine CK D) | 15.0% | 7.0 | 3,178 |
| TOTAL | 100% | 46.67 | 21,188 |

A slot die coater was employed to treat Texel needle-punched PET roll goods with 7.5% povidone iodine solution. The treated roll was cut and folded in line to make 8-inch by 6-inch wipes with a 0.65 gram add-on of the povidone iodine solution.

An evaluation of the antimicrobial effectiveness of the povidone iodine washcloth for use as a Health Care Personnel Hand Wash was carried out. Twelve subjects washed their wet hands pre-contaminated with 5 ml of *Serratia marcescens* culture with the treated wash clothes for 30 seconds to eliminate or kill the *Serratia marcescens* applied to their hands.

It was concluded that the $Log_{10}$ reduction in CFU per hand achieved by the test article (the 7.5% povidone iodine washcloth) met the FDA's proposed $2.0 \log_{10}$ reduction in CFU per hand following the first wash and $3.0 \log_{10}$ reduction in CFU per hand following the tenth wash.

EXAMPLE #6

This example was developed to evaluate the effects of adding a re-fatting or solubilizing agent called Softigen® 767, an ethoxylated product of partial glycerides with fatty acids derived from coconut and palm kernel oil, chemically known as Caprylocaproyl Polyoxylglycerides, or PEG-6-Caprylic/Capric Glycerides, to the treatment formulation that has also been modified to reduce the surfactant concentration from 16% to 10%. These modifications were done to provide for the higher frequency of use of antiseptic hand washes by health care personnel as needed to prevent nosocomial infections, and the skin irritation and dryness that the regimen can cause.

The following Formulation #6 was slot-coated onto a 70 GSM, 100% PET non-woven needle-punched material, from Texel, at the rate of 0.65 grams per 6-inch by 8-inch wipe:

| Formulation # 6 | |
|---|---|
| Wt. Percent | Ingredients |
| 7.5% | Povidone iodine |
| 78.5% | Propylene glycol |
| 10.0% | Cocamidopropyl betaine (Tego ® Betaine CK D) |
| 4.0% | Softigen ® 767[1] |

[1]Softigen ® 767 is a surface active, water soluble clear liquid which serves as refatting and solubilizing agent in cosmetic and pharmaceutical formulations - Sasol Germany GmbH, Arthur-Imhausen-Str. 92, 58453 Witten, Germany.

The evaluation consisted of thoroughly wetting both hands with water, then using the treated wipes to absorb the 4 to 6 grams of water on the wetted hands to activate the wipes to gently scrub both hands for at least 30 seconds. Significantly, there was no apparent diminishing of foaming action and the hands felt smooth with no tacky after-feel. The above test evaluations were repeated four times over a one-hour period, by two lab technicians, with comparable results.

When the PVP-I was omitted and the Tego® Betaine was introduced into the propylene glycol and the solution was heated to under 110° F. while stirring, the resultant solution introduced by slot coating the fabric (0.62 and 0.80 add-on), and the integrated fabric wetted with water and used on the hands, strong foaming was observed. It was established that a cleaning and de-germing had taken place following removal of the foam with water.

The invention claimed is:

1. A wipe comprising a flexible, substantially dry matrix having a moisture content of less than 1% comprising a matrix of synthetic, woven, non-woven or knitted fibers containing 100% of polypropylene or polyester fiber or a mixture comprising 50-70% polypropylene and 30-50% polyester fibers, said matrix being coated or impregnated with an antimicrobial treatment solution, said treatment solution containing less than 1% of water and including about 1.0 to about 15% by wt. of polyvinyl pyrrolidone iodine as antimicrobial or antiseptic and 0.5 to 25% by weight of spray dried cocamidopropyl betaine in a non-aqueous solvent carrier selected from the group consisting of glycol, glycerin and mixtures thereof.

2. The wipe of claim 1 wherein said non-aqueous solvent carrier is a glycol.

3. The wipe of claim 1 in which said non-aqueous solvent carrier is propylene glycol and is present in said treatment solution in an amount between 25% by weight and 80% by weight of said treatment solution.

4. The wipe of claim 1 wherein said non-aqueous solvent carrier is a mixture of propylene glycol and glycerin.

5. The wipe of claim 1 in which there is additionally present a nonionic or a cationic surfactant or a mixture thereof.

6. The wipe of claim 5 in which said non-ionic or cationic surfactant is present in an amount of less than 40% by wt. of the matrix.

7. The wipe of claim 5 wherein said non-ionic or cationic surfactant is present in an amount of about 0.50% by wt. to about 15% by wt. of the treatment solution.

8. The wipe of claim 1 wherein said treatment solution contains a fragrance.

9. The wipe of claim 1 wherein said matrix is substantially binder free.

10. The wipe of claim 1 wherein said treatment solution contains a moisturizer.

11. A method of sanitizing skin comprising the steps of
   a. wetting a wipe according to claim 1 with water,
   b. wiping the skin using the water activated wipe, and
   c. rinsing the skin with water.

12. A method for producing the wipe according to claim 1, comprising impregnating said fabric by slot coating with said treatment solution, and cutting and folding said coated fabric.

13. A method for sanitizing skin which comprises wetting the skin and then scrubbing the skin with a wipe according to claim 1 to produce a solution of the composition contained in the wipe on the skin and rinsing the skin to remove the solution and the killed bacteria, microbes, fungi and residual debris.

* * * * *